US008540995B2

(12) United States Patent
Mookkan et al.

(10) Patent No.: US 8,540,995 B2
(45) Date of Patent: Sep. 24, 2013

(54) MONOCLONAL ANTIBODIES SPECIFIC TO THE FUSION PEPTIDE FROM HEMAGGLUTININ FROM INFLUENZA A VIRUSES AND USES THEREOF

(75) Inventors: Prabakaran Mookkan, Singapore (SG); Nayana Prabhu Padubidhri, Singapore (SG); Sumathy Velumani, Singapore (SG); Hwei-Sing Jimmy Kwang, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 124 days.

(21) Appl. No.: 13/141,160

(22) PCT Filed: Dec. 24, 2008

(86) PCT No.: PCT/SG2008/000499
§ 371 (c)(1),
(2), (4) Date: Jun. 21, 2011

(87) PCT Pub. No.: WO2010/074656
PCT Pub. Date: Jul. 1, 2010

(65) Prior Publication Data
US 2011/0256141 A1  Oct. 20, 2011

(51) Int. Cl.
*A61K 39/42* (2006.01)
*C12Q 1/70* (2006.01)
*C07K 16/10* (2006.01)

(52) U.S. Cl.
USPC .......... 424/147.1; 424/130.1; 435/5; 435/7.1; 530/387.1; 530/388.3

(58) Field of Classification Search
None
See application file for complete search history.

(56) References Cited

U.S. PATENT DOCUMENTS

| 6,720,409 B2 | 4/2004 | Okuno et al. |
| 2007/0243629 A1 | 10/2007 | Angstrom et al. |
| 2008/0260762 A1 | 10/2008 | Grey et al. |

FOREIGN PATENT DOCUMENTS

| WO | 2005021574 A2 | | 3/2005 |
| WO | 2007082734 A2 | | 7/2007 |
| WO | WO 2007/082734 | * | 7/2007 |
| WO | 2007089753 A2 | | 8/2007 |
| WO | 2008028946 A2 | | 3/2008 |
| WO | 2008140415 A1 | | 11/2008 |

OTHER PUBLICATIONS

Gocnik et al. J Gen Virol Mar. 2007 vol. 88, pp. 951-955.*

* cited by examiner

*Primary Examiner* — Mary E Mosher
*Assistant Examiner* — Myron Hill
(74) *Attorney, Agent, or Firm* — Rothwell, Figg, Ernst & Manbeck P.C.

(57) ABSTRACT

This invention relates to methods and products for the diagnosis, surveillance, prevention, and treatment of influenza A virus infections in animals and humans. More particularly, the invention relates to antibodies and related binding proteins for the detection, prevention and treatment of influenza A viruses. The monoclonal antibodies and related binding proteins of the invention are useful for the treatment of the highly pathogenic H5 subtypes of avian influenza virus (AIV).

29 Claims, 14 Drawing Sheets a.
```
1  285————————345
2  285——————————————360
3  285————————————————375
4  285———————————————————390
5  285——————————————————————405
6  285—————————————————————————420
7           361——————————435
8           361—————————————450
9           361————————————————465
10          361———————————————————480
11                    421——————————495
12                    421—————————————510
13                    421————————————————525
14                    421———————————————————540
HA2  331——————————————————————————————————540
```

US 8,540,995 B2

MONOCLONAL ANTIBODIES SPECIFIC TO THE FUSION PEPTIDE FROM HEMAGGLUTININ FROM INFLUENZA A VIRUSES AND USES THEREOF

This application is a filing under 35 USC 371 of PCT/SG2008/000499, filed Dec. 24, 2008 and published as WO 2010/074656 on Jul. 1, 2010. This prior application is incorporated herein by reference.

FIELD OF THE INVENTION

This invention relates to methods and products for the diagnosis, surveillance, prevention, and treatment of influenza A virus infections in animals and humans. More particularly, the invention relates to antibodies and related binding proteins for the detection, prevention and treatment of influenza A viruses. The monoclonal antibodies and related binding proteins of the invention are useful for the treatment of the highly pathogenic H5 subtypes of avian influenza virus (AIV).

BACKGROUND OF THE INVENTION

Highly Pathogenic avian Influenza (HPAI) H5 strains are currently causing major morbidity and mortality in poultry populations across Asia, Europe, and Africa and have caused 385 confirmed human infections, with a fatality rate of 63.11% (1, 2)[1]. Preventive and therapeutic measures against circulating H5N1 strains have received a lot of interest and effort globally to prevent another pandemic outbreak. Influenza A virus poses a challenge as it rapidly alters its appearance to the immune system by antigenic drift (mutating) and antigenic shift (exchanging its components) (3). The current combat strategies against influenza include vaccination and anti-viral drug treatment, with vaccination being the preferred option. The annual influenza vaccine aims to stimulate the generation of anti-hemagglutinin neutralizing antibodies, which confer protection against homologous strains. The current vaccines have met with varying degrees of success (4). The fact that these strategies target the highly variable HA determinant and predicting the major HA types that pose the next epidemic threat, can impose limitations to the current viral strategy. In the absence of an effective vaccine, therapy is the mainstay of control of influenza infection. Therefore, therapeutic measures against influenza will play a major role in case a pandemic arises due to H5 strains. Currently licensed anti-viral drugs include the M2 ion channel inhibitors (Rimantidine and Amantidine) and the neuraminidase inhibitors (Oseltamivir and Zanamivir). The H5N1 viruses are known to be resistant to the M2 ion channel inhibitors (5, 6). Newer strains of H5N1 viruses are being isolated which are even resistant to the neuraminidase inhibitors (Oseltamivir and Zanamivir) (3, 7). The neuraminidase inhibitors also may need high doses and prolonged treatment (3, 8). Hence, alternative strategies for treatment of influenza are warranted. Recently, passive immunotherapy using monoclonal antibodies are being viewed upon as a viable treatment option (9).

[1] A bibliography is provided at the end of the disclosure.

Testing during an outbreak of an acute respiratory disease can determine if influenza is the cause. During influenza season, testing of selected patients presenting with respiratory illnesses compatible with influenza can help establish whether influenza is present in a specific patient population and help health-care providers determine how to use their clinical judgment for diagnosing and treating respiratory illness. A rapid influenza test helps in the determination of whether to use an antiviral medication. Some tests, such as a viral culture, reverse-transcriptase polymerase chain reaction (RT-PCR) and serological testing are the routine methods, but results may not be available in a timely manner to assist clinicians. At present, most of the rapid diagnostic tests currently in use are monoclonal antibody-based immunoassays. Immunofluorescence (fluorescent antibody staining) is the alternative to rapid influenza diagnostic tests which can be used in many hospital laboratories and generally can yield test results in 2-4 hours. Above all, specific monoclonal antibody generation is fundamental to most currently used rapid, sensitive and cost-effective diagnostic methods.

Hemagglutinin (HA) is the most variable gene of the influenza virus and also the most promising target for generating antibodies. It is synthesized as a precursor polypeptide HA0, which is post-translationally cleaved to two polypeptides HA1 and HA2 linked by a disulphide bond. Monoclonal antibodies against the HA1 are known to neutralize the infectivity of the virus and hence provide good protection against infection (10). However, they are less efficient against heterologous or mutant strains which are continuously arising due to antigenic shift. Also, there is the risk of escape mutants being generated which could cause annual epidemics and occasional pandemics.

The HA2 N-terminal fusion peptide is the most highly conserved region in HA among all influenza A subtypes (11). This HA2 polypeptide is responsible for the fusion of the virus and the host endosomal membrane during the entry of the virus into the cell (12). Part of the HA2 N-terminal fusion peptide is exposed as a surface loop in the precursor molecule (13, 14). As most HA subtypes are cleaved by extracellular enzymes, this surface loop is accessible to antibody on HA0 expressed in the plasma membrane of infected host cells (15).

It would be very useful to have available monoclonal antibodies which broadly recognize and can treat influenza A viruses, especially H5 viruses.

OBJECTS OF THE INVENTION

An object of this invention is to provide monoclonal antibodies (mAbs) and related binding proteins that bind to influenza A virus, particularly to the HA2 polypeptide of influenza A viruses. The HA2 polypeptide is highly conserved in influenza A subtypes. Thus, mAbs that specifically recognize the HA2 polypeptide will recognize all influenza A subtypes. The specificity of these monoclonal antibodies provides a basis for effective prophylactic and therapeutic agents.

SUMMARY OF THE INVENTION

In accordance with the present invention, a monoclonal antibody that is specific for conformational epitopes of the influenza A hemagglutinin glycoprotein is provided. The HA2 polypeptide represents the highly conserved region of the hemagglutinin across influenza A strains. The monoclonal antibody binds specifically to the antigenically conserved fusion peptide of HA2 and is effective in providing cross-clade protection against influenza A infections.

MAbs that target conserved epitopes are useful for detecting the virus in tissues which have not been pre-treated, such as frozen tissue specimens and other biological tissues and fluids. In particular, a mAb designated 1C9 targets an epitope on HA2 of influenza A virus, for example, AIV subtypes.

Accordingly, this invention comprises a binding protein having substantially the immunological binding characteristics for a conformational HA2 epitope as those of mAb 1C9.

In a further aspect, the invention comprises a method for detecting influenza A virus in a specimen which comprises detecting the binding of the HA2 polypeptide with a mAb or binding protein having substantially the immunological binding characteristics of mAb 1C9. In particular, the invention relates to immunofluorescence assays, immunohistochemical assays and other methods that utilize such binding proteins.

In another aspect, the invention relates to kits for the detection of influenza A virus which comprise binding proteins having substantially the immunological binding characteristics of mAb 1C9.

The invention further relates to methods of treating subjects infected with influenza A virus strain, which comprise administering to such subjects effective amounts of one or more recombinant monoclonal antibodies or binding proteins or fragments thereof having substantially the immunological binding characteristics of mAb 1C9.

The invention further relates to methods of providing cross-clade protection against infection against the fusion peptide of the HA2 glycoprotein which comprise administering to such subjects effective amounts of one or more recombinant monoclonal antibodies or binding proteins or fragments thereof having substantially the immunological binding characteristics of mAb 1C9.

BRIEF DESCRIPTION OF THE DRAWINGS

FIG. 1a represents gene-segments coding for fragments 1 to 14 of HA2. Western Blotting analyses of the monoclonal antibodies were performed to map their respective epitopes (the numbers indicate the amino acid number on HA0).

FIG. 1b. Western blot analysis of the 14 fragments: mAb1C9 was used as the primary antibody. Lane 1 had the protein molecular weight marker. Lanes 2 and 18 show recombinant HA2 gp, Lane 3 shows HA2 from whole virus, Lanes 4 to 17 show the 14 fragments. Only fragments 1 to 6 show positive results, while fragments 7 to 14 show negative results. The samples were run on three different gels but processed identically.

FIG. 1c. The results of Western blot analysis of point mutants also expressed as histidine-fusion peptides. The membrane was developed using ECL reagents. The analysis was carried out to determine the amino acid sequence of the epitope for mAb 1C9. Lanes 1 and 16 had the protein molecular weight marker. Lanes 2 and 17 show the wild-type fragment 1. Lanes 3 to 15, 18 and 19 were loaded with the over expressed point mutants. Positive results were seen only in lanes with wild type fragment 1, point mutants I340A (12), E341A (13), G342A (14), G343A (15), W344A (18) and Q345A (19), indicating the absence of the role of the respective amino acids in binding to the HA2 gp. Negative results were seen in lanes with point mutants G331A (3), L332A (4), F333A (5), G334A (6), A335A (7), I336A (8), A337G (9), G338A (10) and F339A (11), indicating the role of these amino acids in forming the epitope of mAb 1C9. Lane numbers of the respective point mutants are indicated in brackets. The samples were run on two different gels but processed identically.

Clade 2.1) virus. The viral loads were measured in the lungs of the infected animals on days 2, 4 and 10 post challenge. The results are expressed in terms of mean value of log (number of copies)/400 ng of RNA±S.D. (# represents no survival of any animals in the group and & represents undetectable viral numbers; *** p<0.01).

Figure 6A:
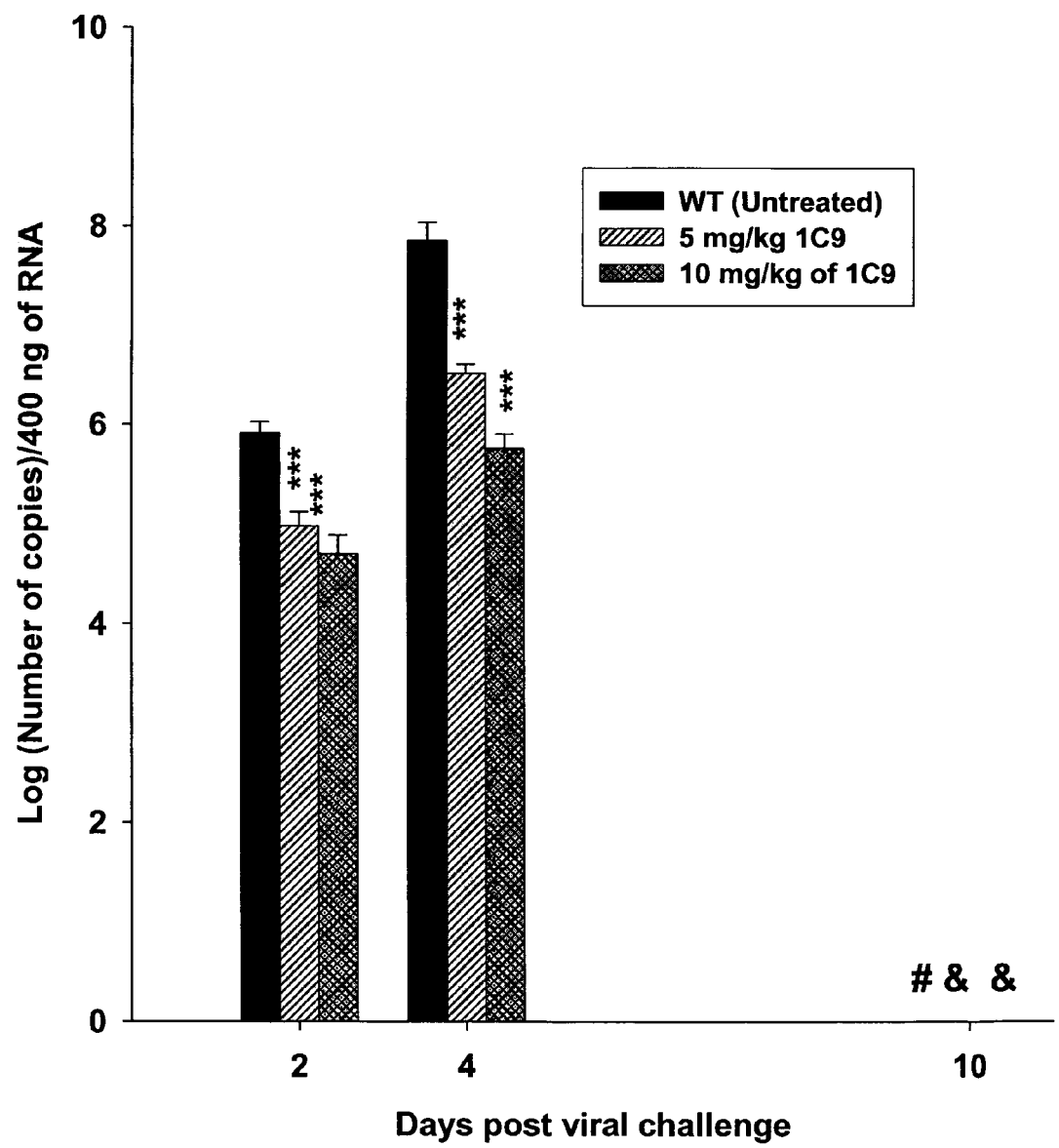
FIG. 6a. shows the measurement of viral loads by qPCR, in the lungs of pre-treated mice and mice challenged with virus. Each group of mice was pre-treated with 10 mg/kg, 5 mg/kg or 0 mg/kg (PBS) of 1C9 mAb on 1 day before challenge with mouse-adapted Indonesian HPAI H5N1 (A/TLL013/06-
Figure 6B:
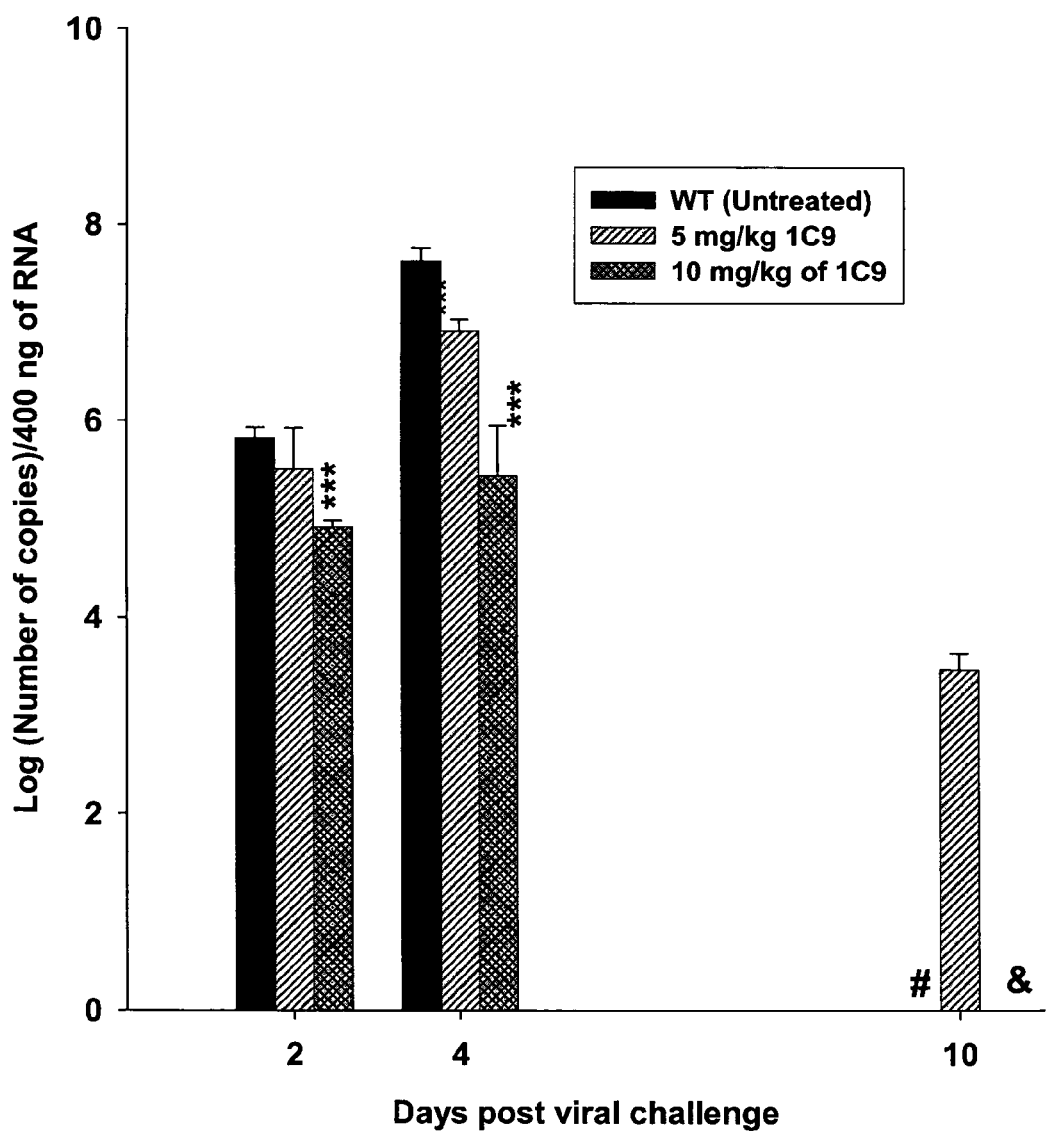

FIG. 6b. shows the measurement of viral loads by qPCR, in the lungs of infected animals challenged with virus and subsequently treated. Each group of mice was challenged with mouse-adapted Indonesian HPAI H5N1 (A/TLL013/06-Clade 2.1) virus and treated with 10 mg/kg, 5 mg/kg or 0 mg/kg (PBS) of 1C9 mAb 1 day after challenge. The viral loads were measured in the lungs of the infected animals on days 2, 4 and 10 post challenge. The results are expressed in terms of mean value of log (number of copies)/400 ng of RNA±S.D. (# represents no survival of any animals in the group and & represents undetectable viral numbers; *** p<0.01).

DETAILED DESCRIPTION OF THE INVENTION

The present invention is directed to mAbs and related antigen-binding proteins that bind specifically to the HA2 N-terminal fusion peptide of influenza A virus. In particular, the mAb or related antigen binding protein possesses the immunological binding characteristics of mAb 1C9, as produced by hybridoma 1C9, deposited with the American Type Culture Collection (ATCC), located at 10801 University Boulevard, Manassas, Va. 20110, USA, under the terms of the Budapest Treaty on Nov. 6, 2007, and assigned Accession Number PTA-8759. The invention further embodies this hybridoma which provides a continuous source of the mAbs and binding proteins of the invention. The invention further relates to methods for the detection and diagnosis of influenza A infection and assay kits that comprise the mAbs or binding proteins of the invention.

The invention further relates to methods of treating a subject infected with an influenza A virus through the administration of effective amounts of an antibody fragment or recombinant antibody comprising an antibody or related binding protein of the invention. In one embodiment the subject is infected with an H5 AIV. The antibody of this invention also can be administered to subjects on the advent of a possible influenza pandemic as a precautionary measure. In this instance, effective amounts of antibody to be administered are about half of the amounts used to treat influenza A virus infections.

Various terms are used herein, which have the following meanings:

The term "immunological binding characteristics" of a mAb or related binding protein, in all of its grammatical forms, refers to the specificity, affinity and cross-reactivity of the mAb or binding protein for its antigen.

The term "binding protein@ refers to a protein, including those described below, that includes the antigen binding site of a mAb of the present invention or a mAb having the immunological binding characteristics of a mAb of the present invention.

The present invention advantageously provides methods for preparing monoclonal antibodies having the binding characteristics of mAb 1C9 by immunizing an animal with an H5N1 virus (A/goose/Guangdong/97). Any such antigen can be used as an immunogen to generate antibodies with the desired immunological binding characteristics. Such antibodies include, but are not limited to, monoclonal antibodies, chimeric antibodies, single chain antibodies, Fab fragments and proteins comprising the antigen binding sequence of mAb 1C9.

The mAb of the present invention can be produced by any technique that provides for the production of antibody molecules by continuous cell lines in culture. Such methods include, but are not limited to, the hybridoma technique originally developed in 1975 by Kohler and Milstein (*Nature* 256:495-497), as well as the trioma technique, the human B-cell hybridoma technique (Kozbor et al., 1983, *Immunology Today* 4:72) and the EBV-hybridoma technique to produce human monoclonal antibodies (Cole et al., in *Monoclonal Antibodies and Cancer Therapy* Alan R. Liss, Inc., pp 77-96 (1985)). Human antibodies can be used and can be obtained by using human hybridomas (Cote et al., 1983, *Proc. Nat=l. Acad. Sci. U.S.A.,* 80:2026-2030) or by transforming human B cells with EBV virus in vitro (Cole et al., 1985, in *Monoclonal Antibodies and Cancer Therapy*, Alan R. Liss, pp. 77-96). Moreover, techniques developed for the production of "chimeric antibodies" or "humanized antibodies" (Morrison et al., 1984, *J. Bacteriol.* 159-870; Neuberger et al., 1984, *Nature* 312:604-608; Takeda et al., 1985, *Nature* 314: 452-454) by introducing sequences from a murine antibody molecule of the present invention, e.g., mAb 1C9, together with genes from a human antibody molecule of appropriate biological activity can be used. Chimeric antibodies are those that contain a human Fc portion and a murine (or other non-human) Fv portion. Humanized antibodies are those in which the murine (or other non-human) complementarity determining regions (CDR) are incorporated into a human antibody. Both chimeric and humanized antibodies are monoclonal. Such human or humanized chimeric antibodies are preferred for use in in vivo diagnosis or therapy of human diseases or disorders.

According to the invention, techniques described for the production of single chain antibodies (U.S. Pat. No. 4,946, 778) can be adapted to provide single chain antibodies of the present invention. An additional embodiment of the invention utilizes the techniques described for the construction of Fab expression libraries (Huse et al., 1989, *Science* 246: 1275-1281) to allow rapid and easy identification of monoclonal Fab fragments with the desired specificity for an antibody of the present invention, or its derivatives, or analogs.

Antibody fragments that contain the idiotype of the antibody molecule can be generated by known techniques. For example, such fragments include but are not limited to: the F(ab=)$_2$ fragment which can be produced by pepsin digestion of the antibody molecule; the Fab=fragments which can be generated by reducing the disulfide bridges of the F(ab=)$_2$ fragment, and the Fab fragments which can be generated by treating the antibody molecule with papain and a reducing agent. Such antibody fragments can be generated from any of the polyclonal or monoclonal antibodies of the invention.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), immunofluorescence assays and immunoelectrophoresis assays, etc. In one embodiment, antibody binding is detected by detecting a label on the primary antibody. In another embodiment, the primary antibody is detected by detecting binding of a secondary antibody or other reagent to the primary antibody. In a further embodiment, the secondary antibody is labeled. Means are known in the art for detecting binding in an immunoassay and are within the scope of the present invention.

The foregoing antibodies can be used in methods known in the art relating to the detection or localization of influenza A viruses, e.g., Western blotting, ELISA, radioimmunoassay, immunofluorescence assay, immunohistochemical assay, and the like. The techniques disclosed herein may be applied to the qualitative and quantitative determination of the HA2 peptide of influenza A viruses and to the diagnosis and surveillance of animals or humans infected with influenza A viruses.

The present invention also includes assay and test kits for the qualitative and/or quantitative determination of the HA2 peptide of influenza A viruses. Such assay systems and test kits may comprise a labeled component prepared, e.g., by labeling with a radioactive atom, a fluorescent group or an enzyme, coupling a label to the mAb or related binding protein of the present invention, or to a binding partner thereof. Such assay or test kits further may comprise reagents, diluents and instructions for use, as is well known to those skilled in immunoassay techniques.

In certain embodiments of the invention, such kits will contain at least the mAb or related binding protein of the invention, means for detecting immunospecific binding of said mAb or related binding protein to AIV in a biological sample, and instructions for use, depending upon the method selected, e.g., "competitive," "sandwich," "DASD" and the like. The kits may also contain positive and negative controls. They may be configured to be used with automated analyzers or automated immunohistochemical slide staining instruments.

An assay kit of the invention can further comprise a second antibody or binding protein that can be labeled or can be provided for attachment to a solid support (or attached to a solid support). Such an antibody or binding protein may be, for example, one that binds to influenza A viruses, particularly AIV. Such second antibodies or binding proteins can be polyclonal or monoclonal antibodies.

Monoclonal antibodies to HA2 peptide of Influenza A hemagglutinin protein can be prepared by immunizing animals with Influenza A virus HA protein or fragments thereof. A preferred method involves amplification of the H5N1 HA0 and HA2 genes followed by expression of the gene, recovery and purification of H5N1 recombinant proteins and use of the purified proteins as immunogens. For example, H5N1 AIV is propagated by inoculation of chicken embryos with available strains of the virus, followed by isolation of the viral RNA. The HA2 gene is amplified by reverse transcriptase polymerase chain reaction (RT-PCR) and then can be cloned into a baculovirus vector that is used to express H5N1 proteins in insect cells. The proteins so produced then can be used to immunize mice or other suitable species for production of hybridomas.

Other immunological methods to detect influenza viruses include, for example, dot-blot and in situ hybridization formats.

The influenza A virus mAb of this invention has advantages over other current methodologies as diagnostic tools. The monoclonal antibody of the present invention can recognize all, or essentially all, influenza A viruses including the highly infectious H5 AIV. Additionally, this mAb provides a safe and convenient diagnostic approach for the detection of influenza A viruses including H5 AIV.

In a further embodiment of the invention, the antibody and related binding proteins of the invention can be administered to treat subjects suffering from an influenza A infection, for example, an infection from an avian influenza virus, such as an H5 subtype, and particularly an H5N1 subtype of AIV. The antibody and related binding proteins of the invention also can be administered to subjects as a preventive measure in the event of an influenza pandemic or threatened pandemic. The antibody and related binding proteins can be administered in a single dose or in repeated administrations, optionally in a slow release form. Administration can be made by any means that enables the antibody to reach its site of action in the body of the subject being treated, e.g., intravenously, intramuscularly, intradermally, orally or nasally. Typically, the antibody is administered in a pharmaceutically acceptable diluent or carrier, such as a sterile aqueous solution, and the composition can further comprise one or more stabilizers, adjuvants, solubilizers, buffers, etc. The exact method of administration, composition and particular dosage will be determined and adjusted at the time of therapy, depending upon the individual needs of the subject, taking into account such factors as the subject=s age, weight, general health, and the nature and extent of his or her symptoms, as well as the frequency of treatment to be given. Generally, the dosage of antibody administered is within the range of about 0.1 mg/kg to about 10 mg/kg body weight when the antibody is administered to treat patients suffering from influenza A infection. Typically, the dosage is reduced by about half, i.e. to within the range of about 0.05 mg/kg to about 5 mg/kg body weight, when administered as a preventive measure.

A single recombinant antibody or binding protein of the invention can be administered for therapeutic purposes or combined with one or more antibodies. Specifically, the antibody of the present invention can be combined with neutralizing antibodies against HA1 protein. If antibodies to one or more generations of neutralization escape mutants have been produced, such antibodies and the 1C9 antibody described above can be administered as therapeutic antibody cocktails The following examples are provided to illustrate a preferred mode of practicing the invention. The invention is not limited to the details of the examples, but is commensurate with the full scope of the appended claims.

Example 1

Production of Hybridomas

CHO-K1 cells and MDCK cells were obtained from American Type Culture Collection. They were cultured in Ham's F12-K medium and Dulbecco's Minimal Essential Medium respectively, both supplemented with 10% fetal bovine serum (FBS), 100 mg/ml streptomycin and 100 units penicillin, and maintained at 37° C., 5% $CO_2$. Avian influenza virus H5N1 (A/goose/Guangdong/97) was inactivated with betapropiolactone and used for RNA extraction to amplify the HA0 gene. The human HPAI H5N1 virus A/Indonesia/TLL013/06 was obtained from Ministry of Health (MOH), Indonesia. The clade 1.0 virus, A/Vietnam/1203/2004 (H5N1) was rescued by reverse genetics. Briefly, the synthesized HA and NA genes were cloned into a dual-promoter plasmid for influenza A reverse genetics (16). Dual-promoter plasmids were obtained from the Center for Disease Control and Prevention, Atlanta, Ga., USA. The reassortant virus was rescued by transfecting plasmids containing HA and NA together with the remaining six gene plasmids derived from A/Puerto Rico/8/34 (H1 N1) into co-culture of 293T and MDCK cells using Lipofectamine 2000 (Invitrogen Corp). After 72 h of transfection, culture medium from the transfected cells was inoculated into 11 day-old embryonated chicken eggs or MDCK cells. The HA and NA genes of reassortant viruses were sequenced to confirm presence of introduced HA and NA genes.

The viruses were propagated in the allantoic cavity of 11 day old chicken embryos and the allantoic fluid was harvested from the eggs after 48 h. Virus titers were determined using hemagglutination assays (17). The virus was then clarified and stored at −80° C. All experiments with live viruses were performed in a biosafety level 3 containment laboratory and all the animal experiments were carried out in an Animal biosafety level 3 (ABSL3) containment laboratory in compliance with CDC/NIH and WHO recommendations (18, 19) and also were approved by the Agri-Food and Veterinary Agency (AVA) and MOH, Singapore.

The total RNA was extracted from H5N1 (A/goose/Guangdong/97) by using Trizol (Invitrogen, USA). The HA0 gene and the HA2 gene were amplified from the cDNA and cloned into pQE-30 vector (Qiagen, Germany) using standard cloning techniques for expression in bacteria. The clones were transformed into *Escherichia coli* M15 pREP4 competent cells to express the protein. The transformed *E. coli* M15 cells were grown at 37° C. to an $OD_{600}$ of 0.5-0.6 in Luria-Bertani (LB) medium containing ampicillin (100 μg/ml) and protein expression was induced by the addition of 1 mmol/L IPTG for 3 h with shaking. The histidine tagged protein was purified on Ni-NTA column (Qiagen, Germany) using standard protocols.

BALB/c mice were immunized two times subcutaneously at regular intervals of 2 weeks with 25 μg of recombinant H5N1 HA0 antigen in 0.1 ml of Phosphate Buffered Saline (PBS), which was emulsified with an equal volume of adjuvant (SEPPIC, France). Thereafter, mice were boosted intravenously with 25 μg of recombinant antigen 3 days before the fusion of splenocytes with SP2/0 cells (20). The fused cells were seeded in 96-well plates, and their supernatants were screened by immunofluorescence assays as described below. Positive clones were checked for isotype by using a one-minute isotyping kit (Amersham Bioscience, England) as described in the manufacturer's protocol.

Example 2

Screening of mAbs by IFA

Sf-9 and MDCK cells in 96-well plates were infected with recombinant baculovirus harboring the truncated H5N1 HA1 and HA0 gene, or with AIV H5N1 Indonesian strains, H5N2 and H5N3 strains, respectively. At 36 h (for Sf-9 cells) and 24-48 h (for MDCK cells) post-infection, the cells were fixed with 4% para-formaldehyde for 30 min at room temperature and washed thrice with PBS, pH 7.4. The fixed cells were incubated with hybridoma culture fluid at 37° C. for 1 h. Cells were rinsed thrice with PBS and incubated with a 1:40 dilution of fluorescein isothiocyanate (FITC)-conjugated rabbit anti-mouse Ig (Dako, Denmark). Cells were rinsed again in PBS, prior to scoring results in an epifluorescence microscope (Olympus, Japan) with appropriate barrier and excitation filters for optimized FITC visualization (21).

Figure 1:
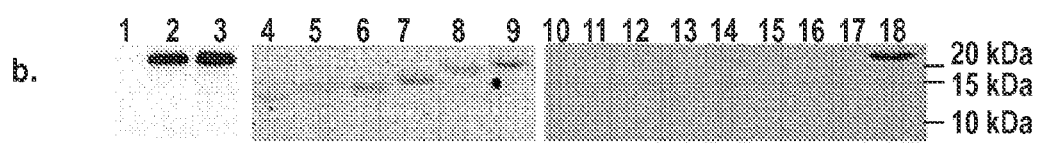
FIGS. 1a-1c show the epitope mapping of monoclonal antibodies 1C9.
Figure 1:
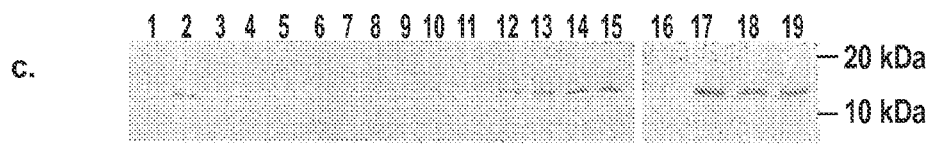
Figure 2:
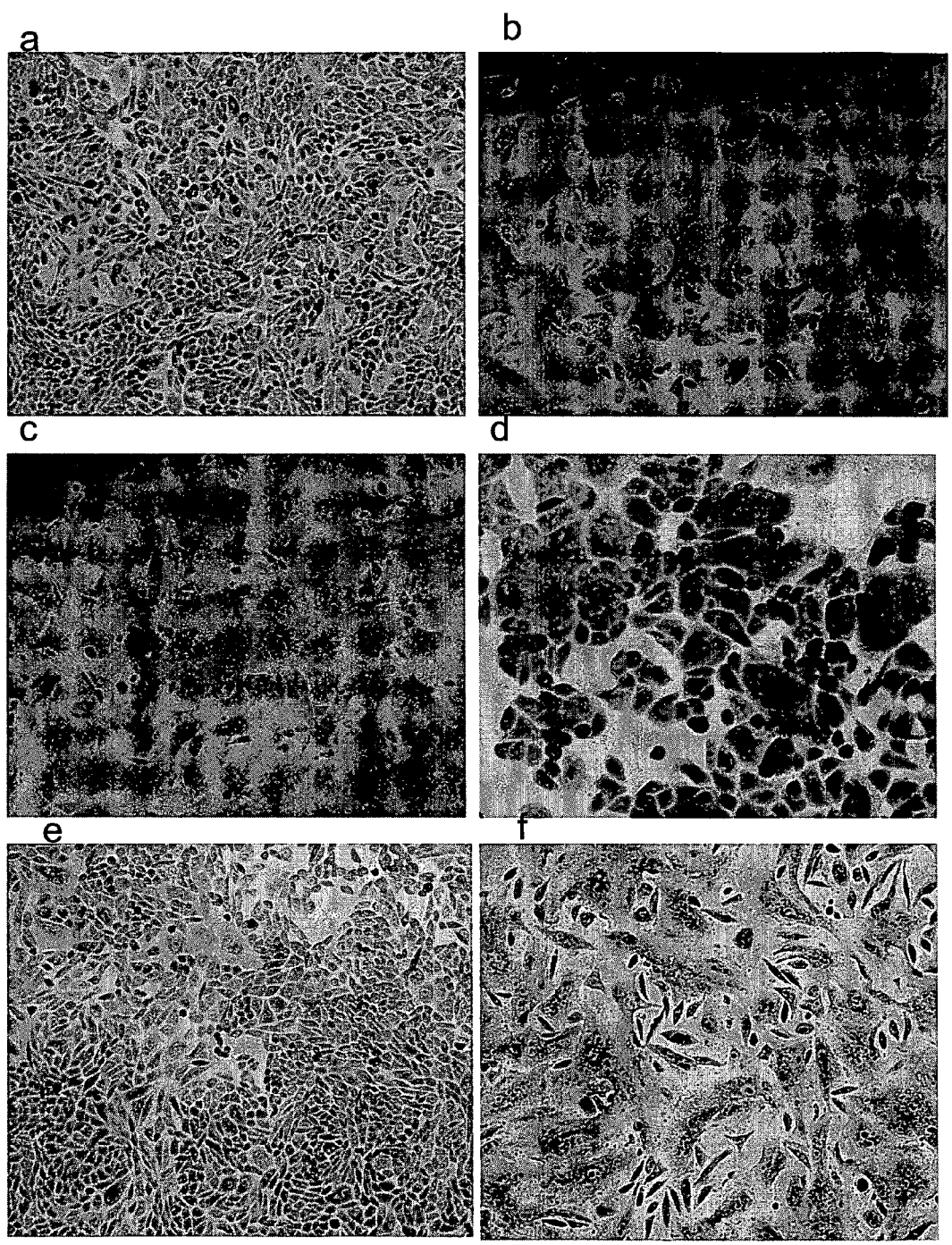
FIG. 2. Inhibition of cell to cell fusion of CHO cells expressing the HA0 precursor. (a) Cells without trypsin treatment, following pH5 treatment, (b) cells after trypsin treatment and following pH5 treatment, (c) cells after trypsin treatment and following pH5 treatment in the presence of 10 μg/ml of mAb 1C9, (d) in the presence of 50 μg/ml of mAb 1C9, (e) in the presence of 100 μg/ml of mAb 1C9, (f) in the presence of 100 μg/ml of non-specific mAb 3H5.

The monoclonal antibody 1C9, which was positive by IFA and immunoblotting, was chosen for epitope mapping. A total of 14 clones expressing fragments of HA2 with sequentially increasing number of amino acids were generated (FIG. 1). The cell lysates, after protein induction, from these clones were run on a SDS-PAGE and Immunoblotting analysis using the anti-HA2 mAbs showed mAb 1C9 was positive to the fragments number 1-6 and negative to all the other fragments (FIG. 1b). With this, it was concluded that the mAb 1C9 recognized an epitope containing amino acids 331 to 345 of HA0 (1-15 of HA2). To further map the epitope of mAb 1C9, several point mutants were generated which altered each of the amino acids in the approximately mapped epitope region, viz. amino acids 331-345 for mAb1C9. Further expression of the point mutants and immunoblotting analyses were carried out. The results showed positive results with mutants 1340A, E341A, G342A, G343A, W344A and Q345A. The mutants G331A, L332A, F333A, G334A, A335G, I336A, A337G, G338A and F339A showed negative results on the western blot (FIG. 1c). These data indicate that the mutants of the amino acids which showed negative results are the ones which are involved in the epitope and hence upon being mutated, were not recognized by the mAb 1C9. The other mutants were recognized by the mAb in spite of the point mutations. These data indicate that mAb 1C9 recognizes an epitope comprising the amino acids 'GLFGAIAGF' (331-339). The mAb 1C9 was against the HA1/HA2 joining region, specifically, against a part of the fusion peptide.

Example 3

Screening Effect of mAbs on HA0 Conformational Change

The HA0 precursor of influenza A hemagglutinin was expressed on the surface of CHO-K1 cells. Upon treatment with trypsin and low pH, the HA0 undergoes a conformational change from the native to the fusion active form resulting in polykaryon formation. Normal polykaryon formation was observed in the control well. The formation of polykaryon was completely inhibited by mAb 1C9 at a concentration of 100 μg/ml and partially at a concentration of 50 μg/ml. An irrelevant monoclonal antibody 3H5 did not show any inhibition of polykaryon formation.

Example 4

Therapeutic Efficacy of the Anti-HA2 mAb Against H5N1 Infection

Figure 4A:
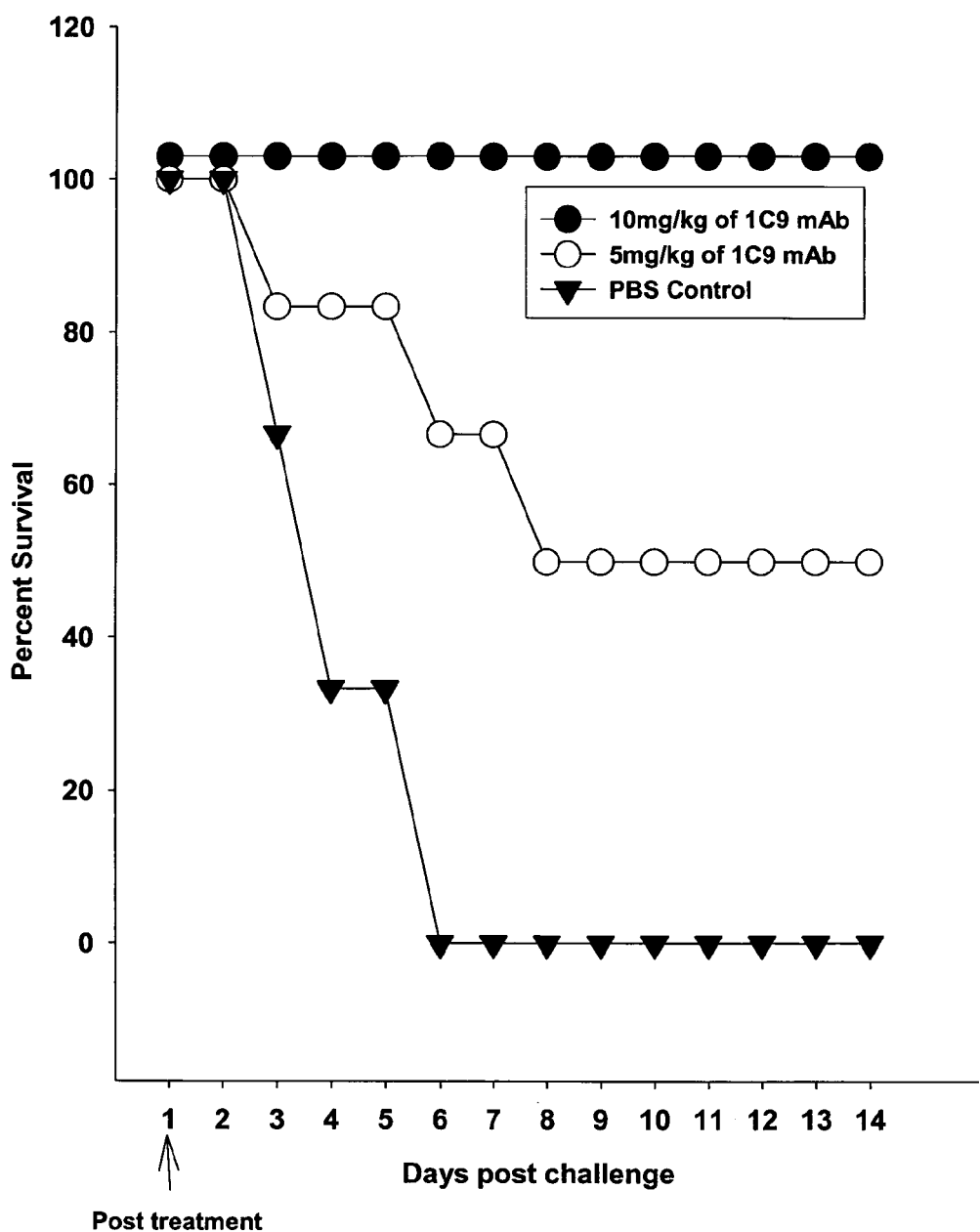
FIG. 4a. Protection of mice from lethal H5N1 viral challenge. Each group of mice was intra-peritoneally treated with 10 mg/kg, 5 mg/kg or 0 mg/kg (PBS) of 1C9 mAb after 1 day post viral challenge with mouse-adapted Indonesian HPAI H5N1 (A/Vietnam/1203/04-Clade 1.0) virus. Mice were monitored for survival throughout a 14 day observation period. The results are expressed in terms of percent survival.
Figure 4B:
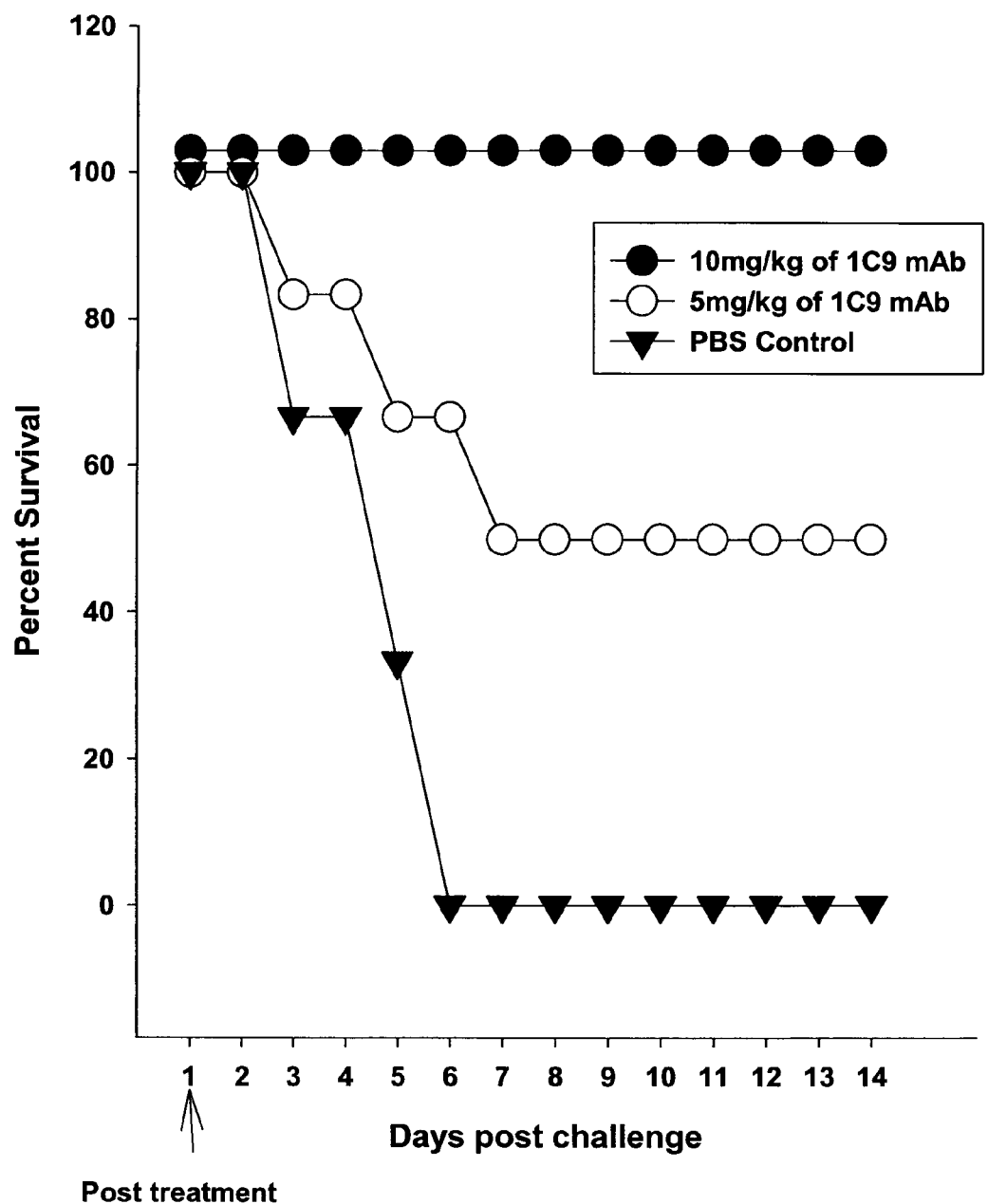
FIGS. 4b and 4c. Protection of mice from lethal H5N1 viral challenge. Each group of mice was intra-peritoneally treated with 10 mg/kg, 5 mg/kg or 0 mg/kg (PBS) of 1C9 mAb after 1 day post viral challenge with mouse-adapted Indonesian HPAI H5N1 (A/TLL013/06-Clade 2.1) virus. Mice were monitored for survival (FIG. 4b) and weight loss (FIG. 4c) throughout a 14 day observation period. The results are expressed in terms of percent survival and percent body weight (at the beginning of the trial), respectively (* represents no survival of any animals in the group).
Figure 4C:
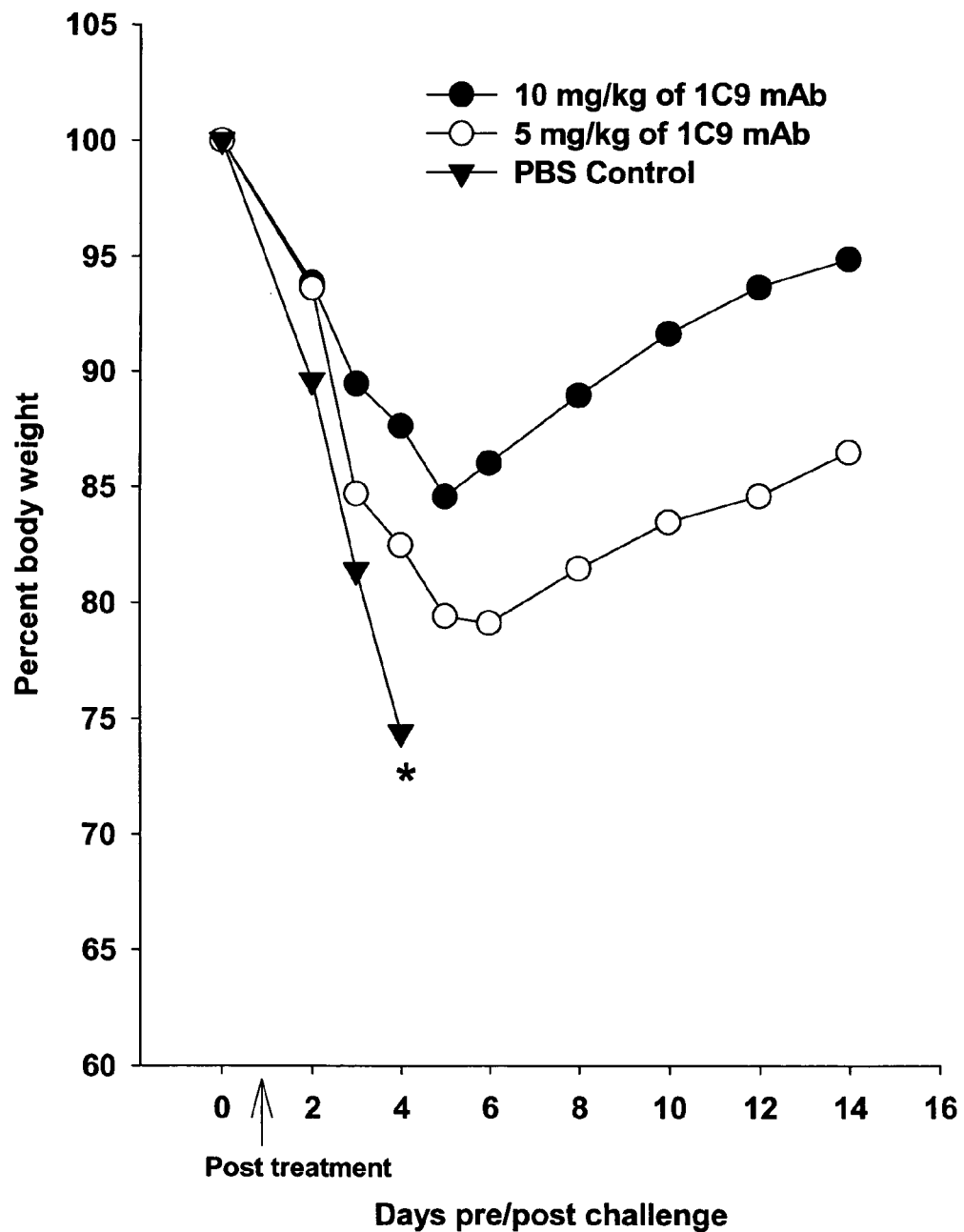

To determine the therapeutic efficacy of mAb 1C9, inbred SPF BALB/c mice aged 4-6 weeks were used. Six mice (n=6) per group were anesthetized with Ketamine/Xylazine and intra-nasally infected with 5MLD50 (Mouse lethal dose 50%) of two different H5N1 strains (A/Vietnam/1203/2004 from clade1 and A/Indonesia/TLL013/06 from clade 2.1). Fifty percent mouse lethal dose (MLD50) was determined as previously described by Reed and Muench method (Reed and Muench, 1938). Each group of mice was treated via intra-peritoneal route with 5 mg/kg, 10 mg/kg or 0 mg/kg (PBS) of each anti-HA2 mAb at time points of 1 or 3 days after viral challenge Groups of experimental mice (n=6/group) were treated with indicated dosages of mAb, one or three days post challenge with 5 $MLD_{50}$ of HPAI H5N1 strains from clade 1.0 or clade 2.1. The progress of infection was indicated by varying trends of decrease in body weight in the different groups. In mice challenged with the H5N1 viruses, PBS control group (untreated mice) showed the most rapid decline in body-weight, culminating in 100% mortality within 5 days after viral challenge. The body weight of succumbed mice from this group, on day 3, was below 80% of the original body weight (FIG. 4c). The mice from the group treated one day after infection, with 10 mg/kg of 1C9 mAb showed up to 15% loss of bodyweight and from 5 days after challenge the mice started gradually regaining their bodyweight (FIG. 4c). At high concentrations, mAb1C9 completely protected mice from disease upon challenge with both the clades of H5N1 viruses (FIG. 4b). The mice showed ~23% loss of bodyweight and from 4 days after challenge and gradually regained about 8-10% of the lost bodyweight (FIG. 4c). The groups of mice treated with 5 mg/kg of 1C9 showed a loss of body weight less than 22%. The mortality studies showed that this concentration provided 50% protection against 5 $MLD_{50}$ of two H5N1 strains, clade 1.0 (FIG. 4a) and clade 2.1 (FIG. 4b).

Figure 4D:
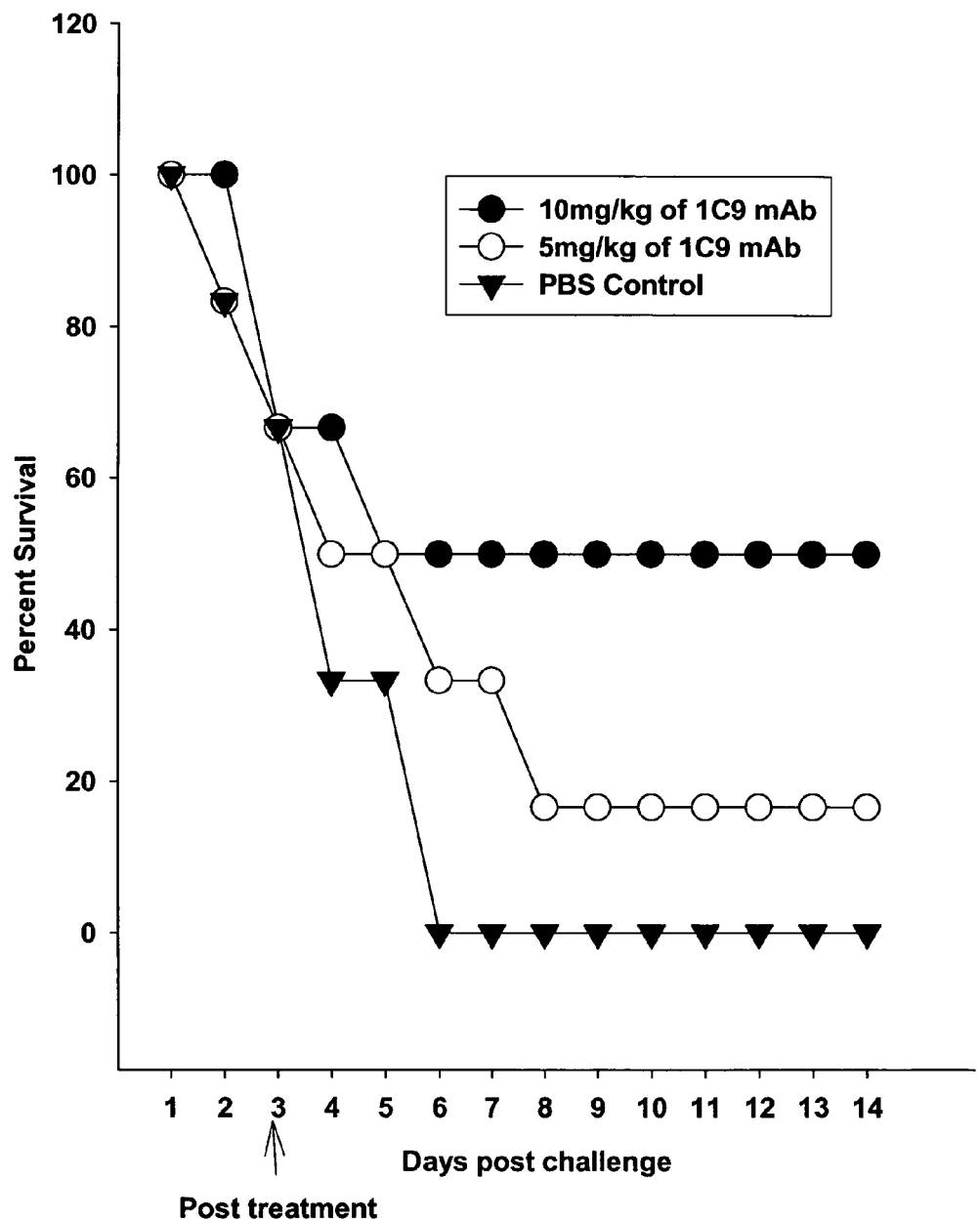
FIG. 4d. Protection of mice from lethal H5N1 viral challenge. Each group of mice were intra-peritoneally treated with 10 mg/kg, 5 mg/kg or 0 mg/kg (PBS) of 1C9 mAb after 3 day post viral challenge with mouse-adapted Indonesian HPAI H5N1 (A/Vietnam/1203/04-Clade 1.0) virus. Mice were monitored for survival throughout a 14 day observation period. The results are expressed in terms of percent survival.
Figure 4E:
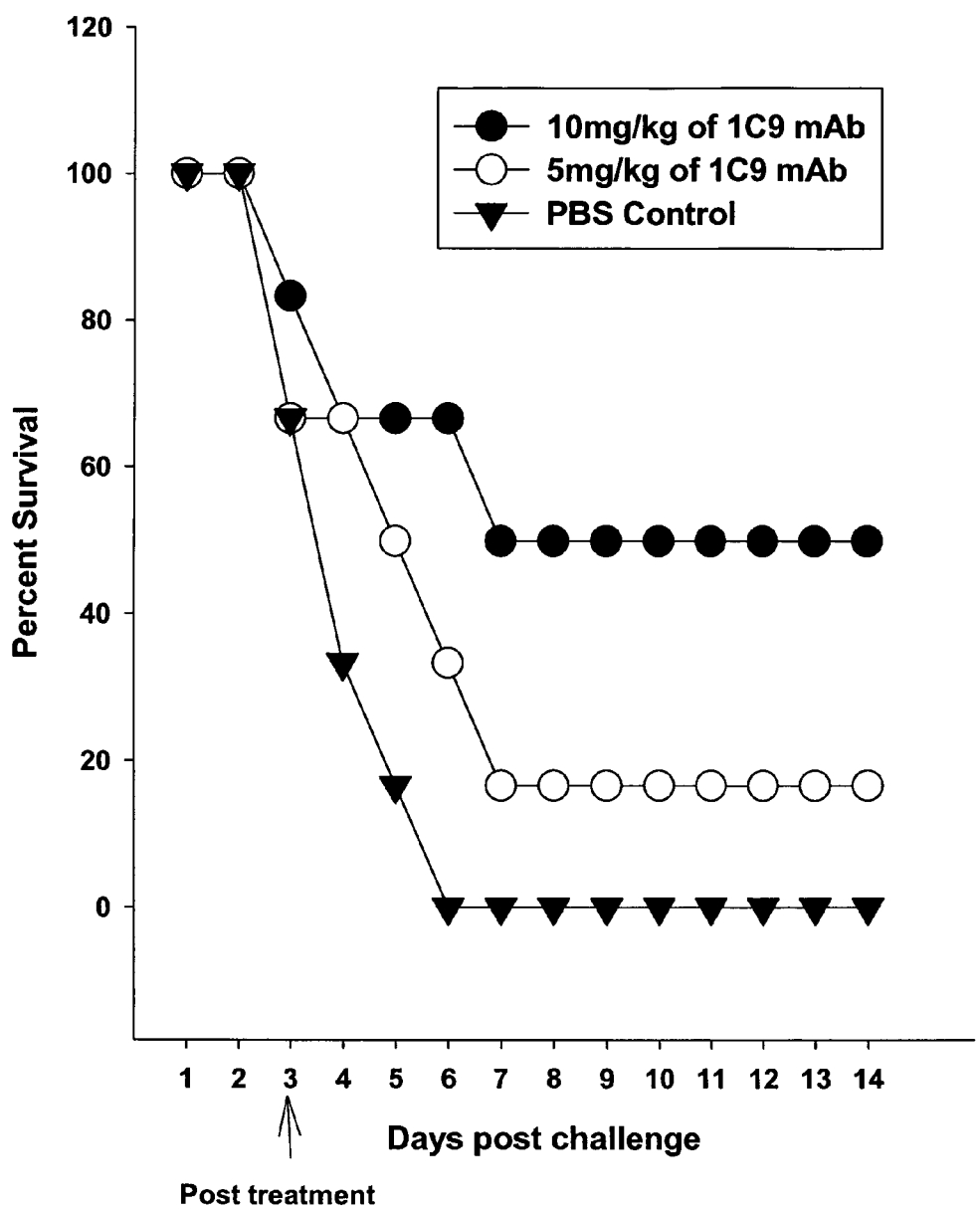
FIGS. 4e and 4f. Protection of mice from lethal H5N1 viral challenge. Each group of mice was intraperitoneally treated with 10 mg/kg, 5 mg/kg or 0 mg/kg (PBS) of 1C9 mAb after 3 day post viral challenge with mouse-adapted Indonesian HPAI H5N1 (A/TLL013/06-Clade 2.1) virus. Mice were monitored for survival (FIG. 4e) and weight loss (FIG. 40 throughout a 14 day observation period. The results are expressed in terms of percent survival and percent body weight (at the beginning of the trial), respectively (* represents no survival of any animals in the group).
Figure 4F:
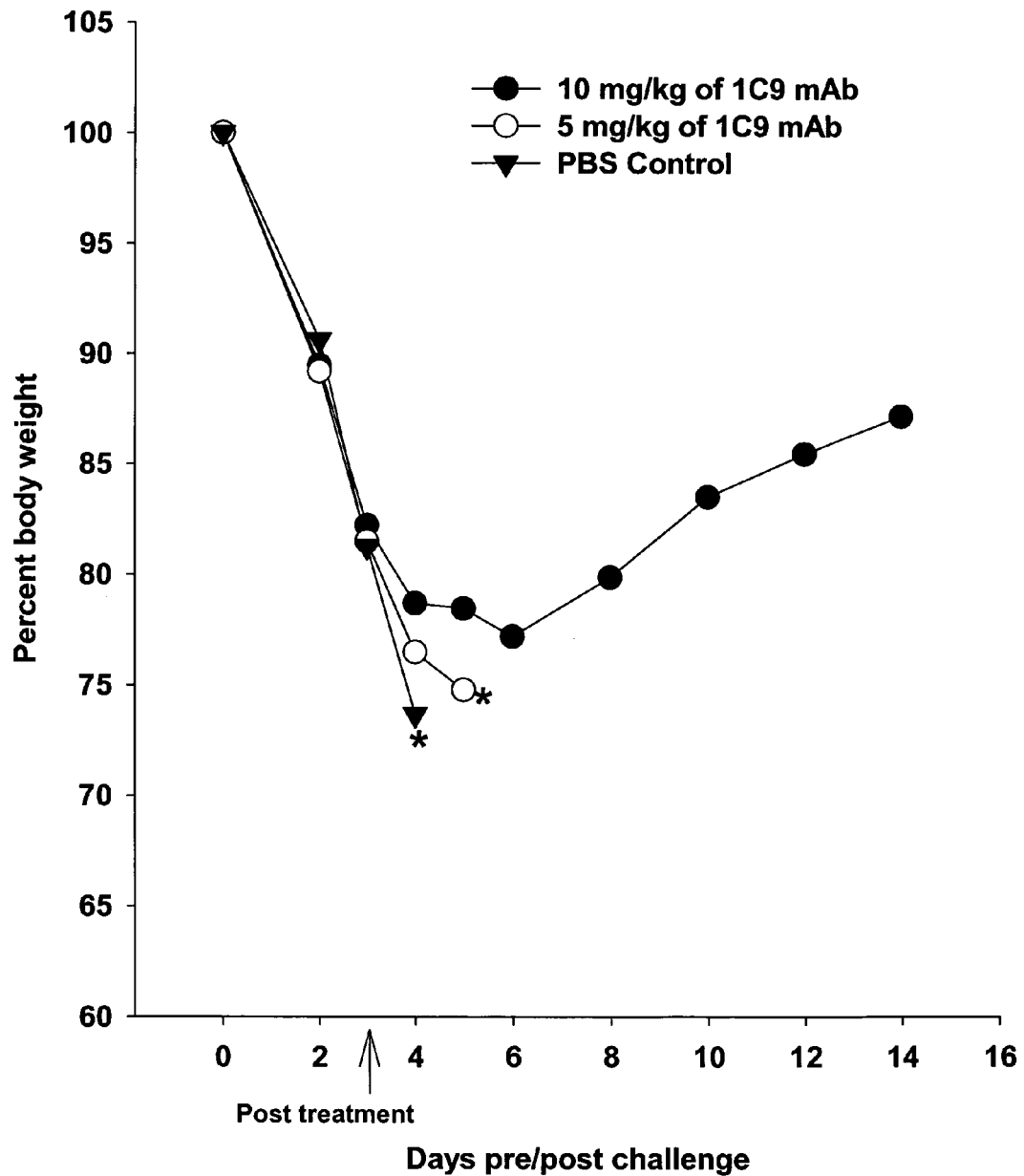

The groups of mice were treated with 1C9 mAb three days post challenge with the two H5N1 strains. Three days after the challenge (before treatment) 16.6-33.3% (1-2 mice out of six/group) of the mice/group died and the therapeutic efficacy of the mAb was tested only in the surviving mice. The 10 mg/kg of 1C9 mAb provided 75% (3 out of 4 mice survived) protection against H5N1 strains (FIG. 4d and FIG. 4e). The 5 mg of 1C9 mAb provided 50% (2 out of 4 survived) protection against $5MLD_{50}$ H5N1 strains (FIG. 4d and FIG. 4e).

Example 5

Prophylactic Efficacy of Anti-HA2 mAb Against H5 Infection

To determine the prophylactic efficacy, a group of mice (n=6/group) was pre-treated with 5 mg/kg, 10 mg/kg or 0 mg/kg (PBS) of mAb 1C9, prior to the viral challenge. After 24 h, mice were challenged with $5MLD_{50}$ of the two different H5N1 strains. Mice were observed daily to monitor body weight and mortality. Monitoring continued until all animals died or until day 14 after challenge.

Figure 5A:
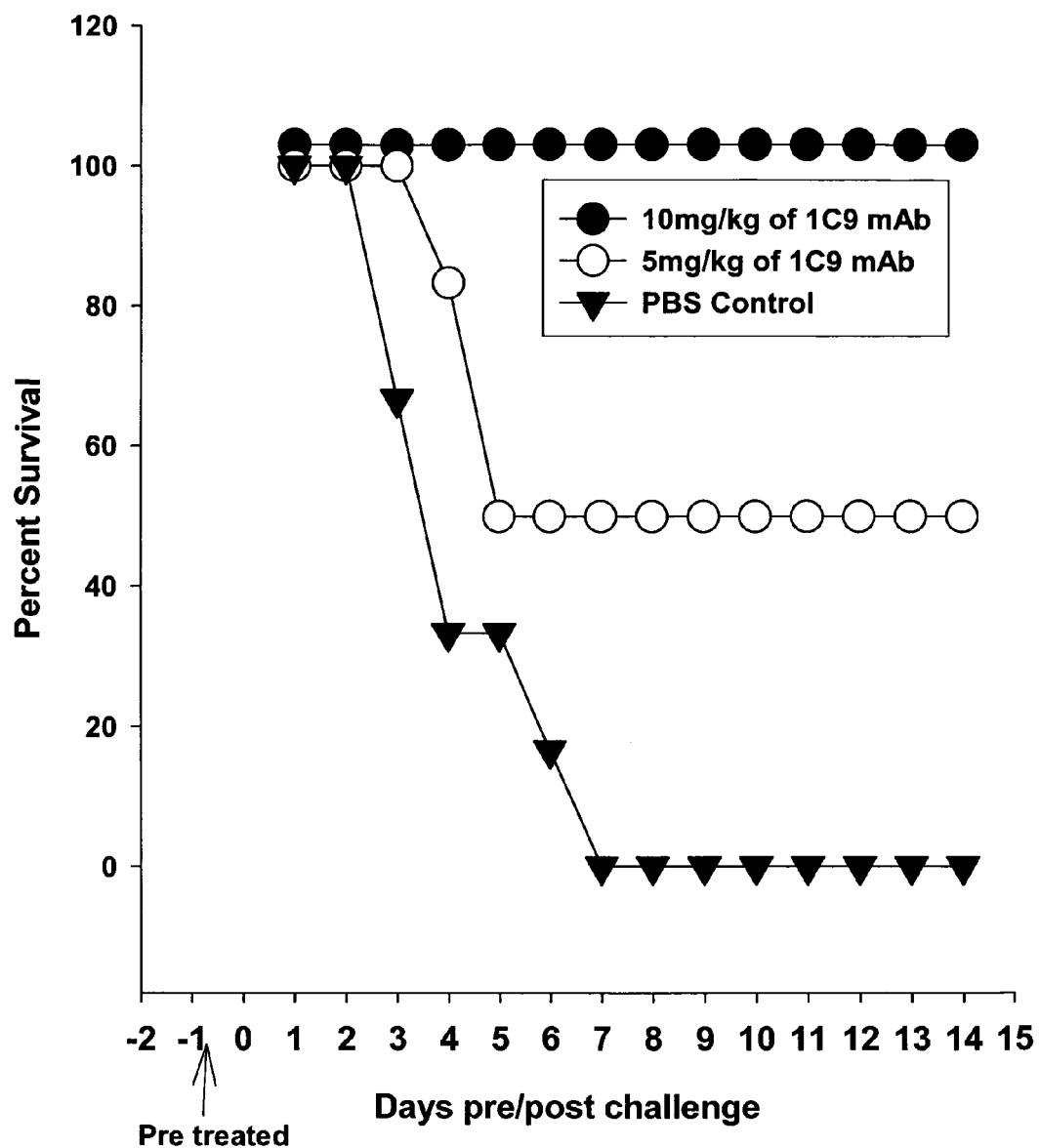
FIG. 5a. Protection of mice from lethal H5N1 viral challenge. Each group of mice were intra-peritoneally pre-treated with 10 mg/kg, 5 mg/kg or 0 mg/kg (PBS) of 1C9 mAb on 1 day before challenge with mouse-adapted Indonesian HPAI H5N1 (A/Vietnam/1203/04-Clade 1.0) virus. Mice were monitored for survival throughout a 14 day observation period. The results are expressed in terms of percent survival.
Figure 5B:
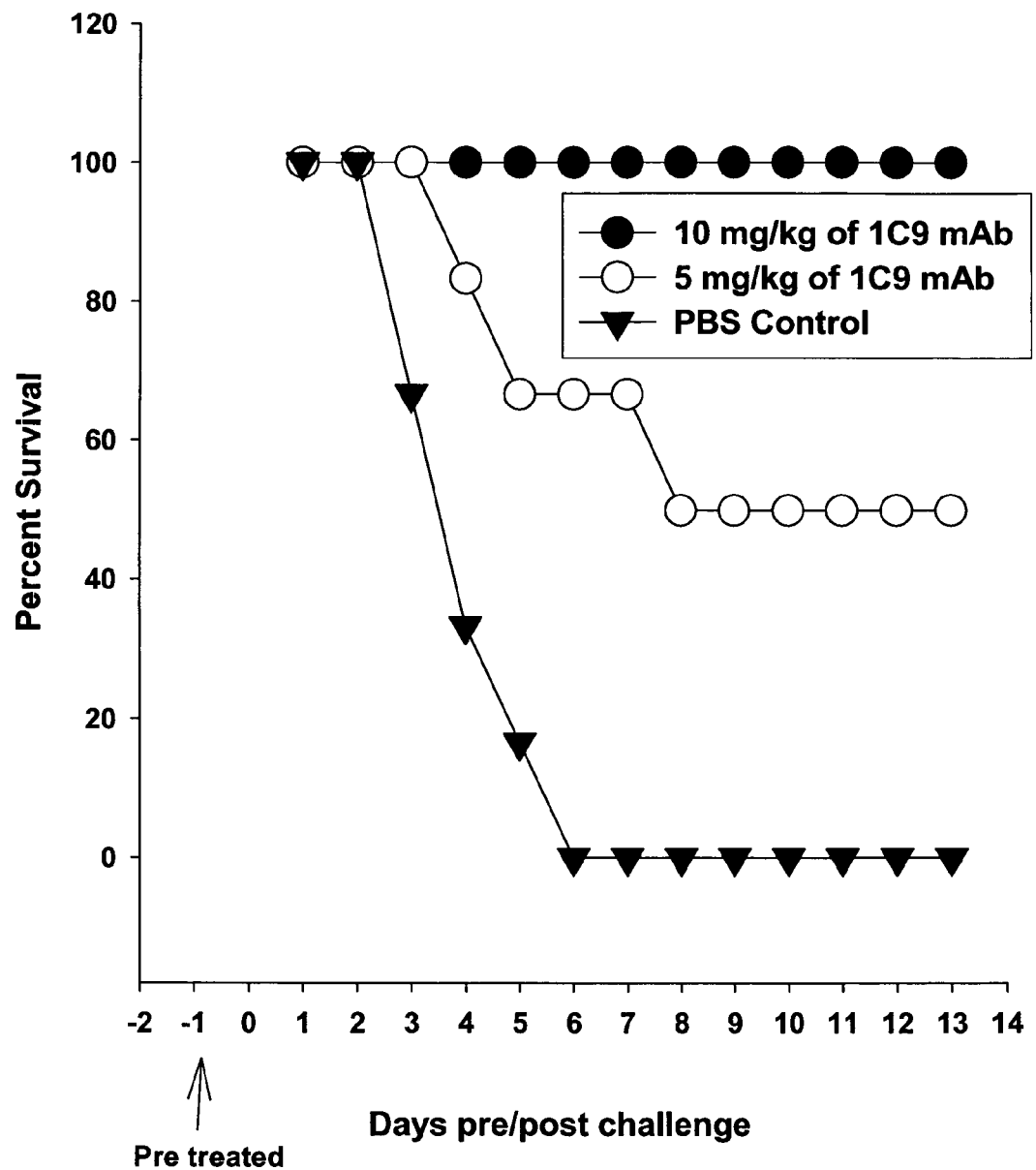
FIGS. 5b and 5c. Protection of mice from lethal H5N1 viral challenge. Each group of mice were pre-treated with 10 mg/kg, 5 mg/kg or 0 mg/kg (PBS) of 1C9 mAb on 1 day before challenge with mouse-adapted Indonesian HPAI H5N1 (A/TLL013/06-Clade 2.1) virus. Mice were monitored for survival (FIG. 5b) and weight loss (FIG. 5c) throughout a 14 day observation period. The results are expressed in terms of percent survival and percent body weight (at the beginning of the trial), respectively (* represents no survival of any animals in the group).
Figure 5C:
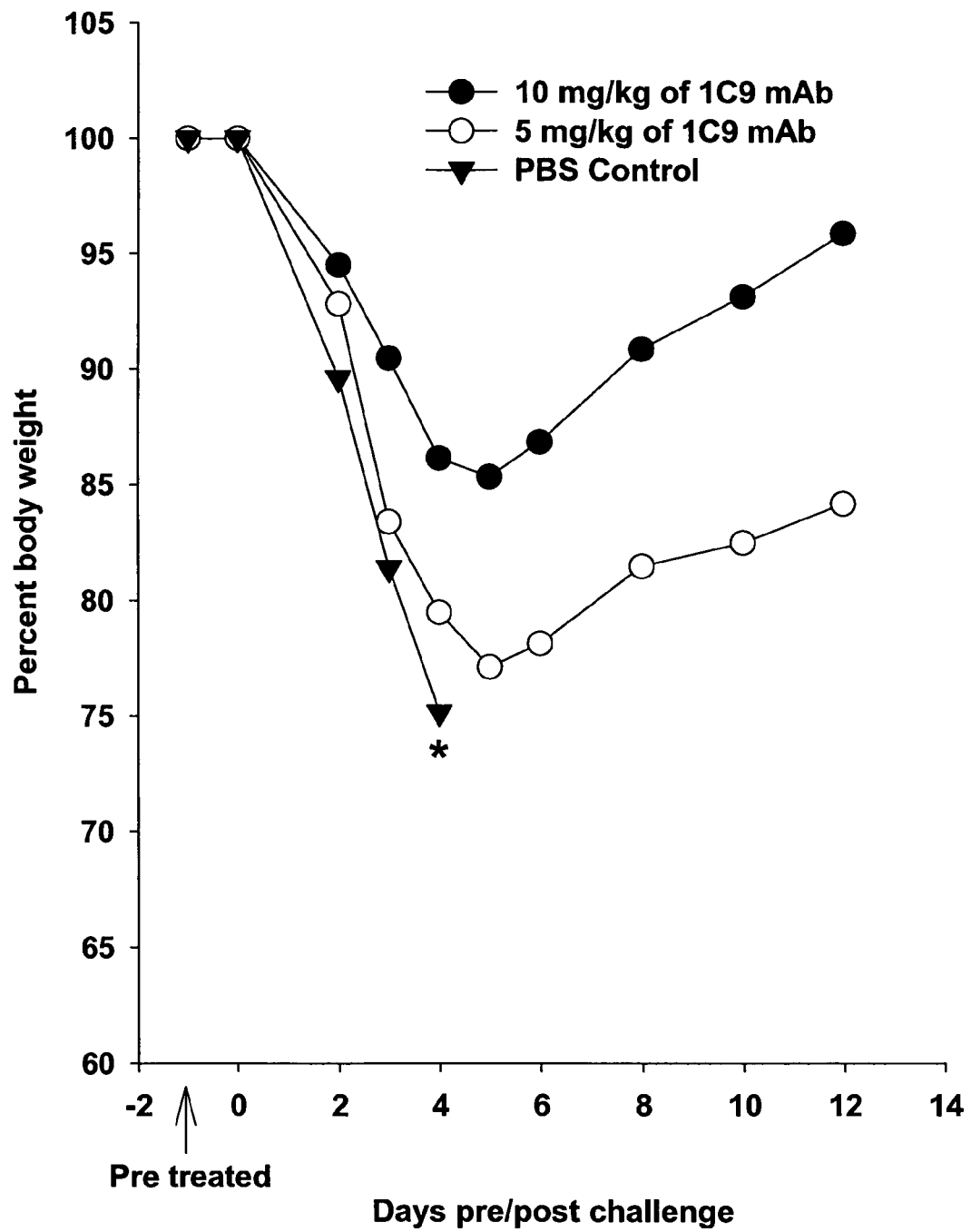

The group of mice pre-treated with 10 mg/kg of 1C9 mAb provided 100% protection against 5 $MLD_{50}$ of two H5N1 strains, clade 1.0 (FIG. 5a) and clade 2.1 (FIG. 5b). This group of mice showed only 15% loss in body weight on day 5 and regained the body weight (FIG. 5c). Pre-treatment with 1C9 mAb at 5 mg/kg provided 50% protection against $5MLD_{50}$ H5N1 viruses from clade 1.0 (FIG. 5a) and clade 2.1 respectively (FIG. 5b).

Example 6

Determination of Viral Load

About 200 µl of the lung homogenates were treated with 1 ml Trizol reagent to extract RNA. Total RNA (400 ng/sample) were used for cDNA synthesis using 20 U of AMV reverse transcriptase (Roche). The cDNA suspension was used for amplification in a quantitative real-time PCR reaction. DyNAmo™ Capillary SYBR Green qPCR kit (Finnzymes) was used in the PCR assay. Briefly, the cDNA was amplified in 20 µl containing, 0.25 µmol of forward primer (5'-GAAAT-CAAACAGATTAGTCCTTGC-3') (SEQ ID NO:1), and 0.25 µmol of reverse primer (5'-CCTGCCATCCTCCCTC-TATAAA-3') (SEQ ID NO:2), and 1X of the DyNAmo master mix. Reactions were performed in a Light Cycler (Roche, Ind., USA) with the following conditions: 10 min at 95° C., followed by 50 cycles of 95° C. for 10 s, 57° C. for 5 s, and 72° C. for 9 s. Fluorescence signals from these reactions were captured at the end of the extension step in each cycle. To determine the specificity of the assay, PCR products were subjected to melting curve analysis at the end of the assay (65 to 95° C.; 0.1° C./s). Plasmids containing the target sequence were used as positive controls. To determine the dynamic range of real-time quantitative PCR, serial dilutions of plasmid DNA containing the target sequence were made and subjected to the real-time quantitative PCR assay. The assay was able to distinguish 10-fold differences in concentration over a range from 1000 to $10^9$ copies, and no signal was observed in the water control. Relative quantification in triplicate for each experimental sample was obtained by using the standard curve method.

A real time polymerase chain reaction assay was used to evaluate the kinetics of the influenza A virus load in the lung samples of the animals infected with clade 2.1. Titers of viruses in the lungs of mice treated with mAb 1C9 24 hours pre-challenge were compared with those for the untreated mice (FIG. 6a). Titers of viruses in the lungs of mice treated with mAb 1C9 24 hours post-challenge were compared with those for the untreated mice (FIG. 6b). Mice receiving 10 mg/kg of 1C9 showed significantly lesser viral load when compared to the untreated mice on day 4 and no virus titer was detected on day 10 post-challenge. Moreover, mice receiving 5 mg/kg of the same mAb showed lesser viral clearance when compared to the mice receiving 10 mg/kg of 1C9 in a dose dependent manner.

Example 7

Histopathology

For histopathology, a lung sample was collected in 10% (wt/vol) buffered formalin solution, embedded in paraffin and sectioned. Sections were stained with hematoxylin and eosin (H/E) and were analyzed for pathology.

Figure 3:
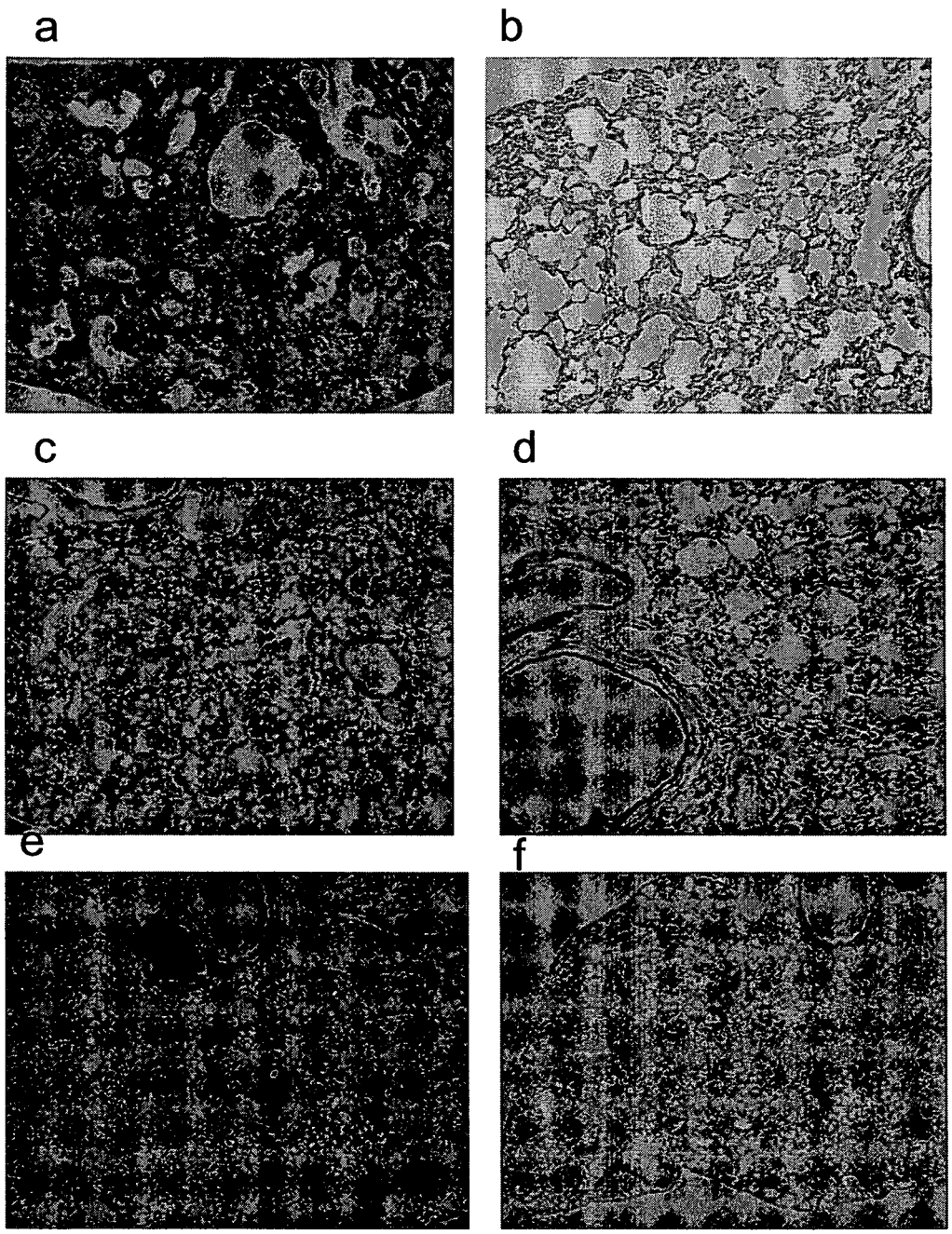
FIG. 3. Photomicrographs of hematoxylin- and eosin-stained lung sections of mice infected with Clade 2.1 H5N1 virus at 5 days post challenge. a) Normal morphology seen in uninfected mice, b) infected and untreated mice, c) infected mice treated with 5 mg/kg of 1C9 at 24 hour post challenge, d) infected mice treated with 10 mg/kg of 1C9 at 24 hour post challenge, e) infected mice treated with 5 mg/kg of 1C9, 24 hours prior to viral challenge, f) infected mice treated with 10 mg/kg of 1C9, 24 hours prior to viral challenge.

Histopathology studies were followed for mice treated with mAb 1C9 24 h pre or post viral challenge. On day 5 p.i., mice infected with the clade 2.1 H5N1 virus had pulmonary lesions consisting of moderate to severe necrotizing bronchitis, moderate to severe histiocytic alveolitis with associated pulmonary edema (FIG. 3b). The uninfected mice lacked lesions in the lungs (FIG. 3a), mice treated (24 h pre or post challenge) with 5 mg/kg of 1C9 had minimal to moderate bronchitis (FIGS. 3c and 3e) and mice treated (24 h pre or post challenge) with 10 mg/kg of 1C9 had minimal bronchitis.

REFERENCES

1. WHO (World Health Organization). Cumulative Number of Confirmed Human Cases of Avian Influenza A/(H5N1) Reported to WHO 10 September 2007. Available at: http://www.who.int/csr/disease/avian_influenza/country/cases_table2008_01_03/en/index.html. Accessed 3 Jan. 2008.
2. No authors listed. 2006. Epidemiology of WHO confirmed human cases of avian influenza A (H5N1) infection. Wkly Epidemiol. Rec. 81: 249-257.
3. de Jong, M. D, and T. T. Hien. 2006. Avian influenza A (H5N1)-Review. J. Clin. Virol. 35: 2-13.
4. Veits. J., A. Romer-Oberdorfer, D. Helferich., M. Durban. M. and et al. 2008. Protective efficacy of several vaccines against highly pathogenic H5N1 avian influenza virus under experimental conditions. Vaccine 26:1688-1696.
5. Beigel, J. H., J. Farrar, A. M. Han, F. G. Hayden, R. Hyer, M. D. de Jong, and et al. 2005. Avian influenza A (H5N1) infection in humans. N. Engl. J. Med. 353:1374-85.
6. Bright, R. A., D. K. Shay, B. Shu, N. J. Cox, and A. I. Klimov. 2006. Adamantane resistance among influenza A viruses isolated early during the 2005-2006 influenza season in the United States. JAMA 295: 891-894.
7. Le, Q. M., M. Kiso, K. Someya, Y. T. Sakai, T. H. Nguyen, and et al. 2005. Avian flu: Isolation of drug-resistant H5N1 virus. Nature 437: 1108.
8. Yen, H. L., A. S. Monto, R. G. Webster, an E. A. Govorkova. 2005. Virulence may determine the necessary duration and 9. Sawyer, L. A. 2000. Antibodies for the prevention and treatment of viral diseases. Antiviral. Res. 47: 57-77
10. Hanson, J. H., C. M. Boon, P. C. Lim, A. Webb, E. E. Ooi, and R. J. Webb. 2006. Passive immunoprophylaxis and therapy with humanized monoclonal antibody specific for influenza A H5 hemagglutinin in mice. Respir. Res. 7:126
11. Gerhard, W., K. Mozdzanowska, and D. Zharikova 2006. Prospects for Universal Influenza Virus Vaccine. Emerging Infect. Dis. 12: 569-574.
12. Lakadamyali, M., M. J. Rust, and X. Zhuang. 2004. Endocytosis of influenza viruses. Microbes Infect. 6: 929-936.
13. Chen, J., K. H. Lee, D. A. Steinhauer, D. J. Stevens, J. J. Skehel, and D. Wiley. 1998. Structure of the hemagglutinin precursor cleavage site, a determinant of influenza pathogenicity and the origin of the labile conformation. Cell 95:409-417.
14. Wilson, I. A., J. J. Skehel, and D. C. Wiley. 1981. Structure of the haemagglutinin membrane glycoprotein of influenza virus at 3 A resolution. Nature 289: 366-373.
15. Atassi, M. Z., and R. G. Webster. 1983. Location, synthesis and activity of an antigenic site on influenza virus hemagglutinin. PNAS 180: 840-844.
16. Horimota, T., A. Takada, K. Fujii, H. Goto, M. Hatta, and et al. 2006. The development and characterization of H5 influenza virus vaccines derived from a 2003 human isolate. Vaccine 24: 3669-3676.
17. Anonymous. 1995. Laboratory biosafety manual. World Health Organization. Ann Ist Super Sanita, 31, 1-121.
18. NIH (National Institutes of Health, U.S.) and CDCP (Centers for Disease Control and Prevention, U.S.) 1999. Biosafety in microbiological and biomedical laboratories, 4th ed. U.S. Dept. of Health and Human Services Public Health Service Centers for Disease Control and Prevention; National Institutes of Health; For sale by the Supt. of Docs. U.S. G.P.O., Washington, D.C.
19. WHO (World Health Organization). 2004. Laboratory biosafety manual, 3rd ed. World Health Organization, Geneva.
20. Yokoyama, W. M. 2001. Production of monoclonal antibody, p. 2.5.1-2.5.17. In J. E. Coligan, A. M. Kruisbeek, D. H. Margulies, E. M. Shevach, and W. Strober (eds.), Current Protocols in Immunology, John Wiley & Sons. Inc., Newcastle, United Kingdom.
21. Velumani, S., Q. Du, B. J. Fenner, M. Prabakaran, and et al. 2008. Development of an antigen-capture ELISA for detection of H7 subtype avian influenza from experimentally infected chickens. J. Virol. Methods 147: 219-225.

The invention claimed is:

1. An antibody that binds specifically to an epitope of a hemagglutinin of H5 subtype of avian influenza A virus and that has the immunological binding characteristics of monoclonal antibody 1C9 as produced by hybridoma 1C9 which is deposited with the American Type Culture Collection with Accession Number PTA-8759, wherein said immunological binding characteristics comprise binding to an epitope that is bound by monoclonal antibody 1C9.

2. The antibody of claim 1 which is a monoclonal antibody, a single chain antibody, an antibody fragment, a chimeric antibody or a humanized antibody.

3. The antibody of claim 1 which is a monoclonal antibody.

4. Monoclonal antibody 1C9 as produced by hybridoma 1C9 which is deposited with the American Type Culture Collection with Accession Number PTA-8759.

5. A method for detecting an influenza A virus in a biological specimen which comprises (a) contacting the specimen with an antibody that binds specifically to an epitope of hemagglutinin of H5 subtype of avian influenza A virus and that has the immunological binding characteristics of monoclonal antibody 1C9 as produced by hybridoma 1C9 which is deposited with the American Type Culture Collection with Accession Number PTA-8759, wherein said immunological binding characteristics comprise binding to an epitope that is bound by monoclonal antibody 1C9 and (b) detecting the binding of said antibody.

6. The method of claim 5 wherein the antibody is a monoclonal antibody, a single chain antibody, an antibody fragment, a chimeric antibody or a humanized antibody.

7. The method of claim 5 wherein the antibody is a monoclonal antibody.

8. The method of claim 7 wherein the monoclonal antibody is antibody 1C9 as produced by hybridoma 1C9 which is deposited with the American Type Culture Collection with Accession Number PTA-8759.

9. The method of claim 5 which further comprises contacting the specimen with a binding protein that specifically binds to an epitope of a glycoprotein of an influenza A virus, wherein said antibody is a capture antibody and the binding protein is a detector binding protein that contains or is conjugated to a detectable element.

10. The method of claim 9 wherein at least one of the antibody and the binding proteins is a monoclonal antibody.

11. The method of claim 9 wherein the antibody and the binding protein are monoclonal antibodies.

12. The method of claim 9 wherein the antibody is immobilized onto a solid surface.

13. The method of claim 9 wherein the binding protein contains a radioactive atom, is conjugated to a fluorescent molecule, or is conjugated to an enzyme.

14. A kit for detecting an influenza A virus in a biological specimen which comprises an antibody that binds specifically to an epitope of hemagglutinin of an H5 subtype of avian influenza A virus and that has the immunological binding characteristics of monoclonal antibody 1C9 as produced by hybridoma 1C9 which is deposited with the American Type Culture Collection with Accession Number PTA-8759, wherein said immunological binding characteristics comprise binding to an epitope that is bound by monoclonal antibody 1C9 together with reagents for the detection of binding of said antibody to said hemagglutinin.

15. The kit of claim 14 which further comprises a binding protein that specifically binds to an epitope of a glycoprotein of an influenza A virus, wherein the antibody is a capture antibody and the binding protein is a detector binding protein that contains or is conjugated to a detectable element.

16. The kit of claim 15 wherein at least one of the antibody and the binding protein is a monoclonal antibody.

17. The kit of claim 15 wherein the antibody and the second binding protein are monoclonal antibodies.

18. The kit of claim 15 wherein the antibody is immobilized onto a solid surface.

19. The kit of claim 15 wherein the binding protein contains a radioactive atom, is conjugated to a fluorescent molecule, or is conjugated to an enzyme.

20. A method of treating a subject infected with an influenza A virus which comprises administering to said subject a therapeutically effective amount of an antibody that binds specifically to an epitope of a hemagglutinin of an H5 subtype of avian influenza A virus and that has the immunological binding characteristics of monoclonal antibody 1C9 as produced by hybridoma 1C9 which is deposited with the American Type Culture Collection with Accession Number PTA-8759, wherein said immunological binding characteristics comprise binding to an epitope that is bound by monoclonal antibody 1C9.

21. The method of claim 20, wherein the antibody is a recombinant monoclonal antibody, single chain antibody, antibody fragment, chimeric antibody or humanized antibody.

22. The method of claim 20, wherein the antibody is monoclonal antibody 1C9 as produced by hybridoma 1C9 which is deposited with the American Type Culture Collection with Accession Number PTA-8759.

23. The method of claim 20, wherein the influenza A virus that infected the subject is an H5 subtype of avian influenza virus.

24. The method of claim 23, wherein the avian influenza virus is an H5N1 subtype.

25. A method of protecting a subject from an influenza A virus infection comprising administering to said subject an antibody that binds specifically to an epitope of hemagglutinin of an influenza A virus and that has the immunological binding characteristics of monoclonal antibody 1C9 as produced by hybridoma 1C9 which is deposited with the American Type Culture Collection with Accession Number PTA-8759, wherein said immunological binding characteristics comprise binding to an epitope that is bound by monoclonal antibody 1C9 in an amount effective to protect the subject from influenza A virus infection.

26. The method of claim 25, wherein the antibody is a recombinant monoclonal antibody, single chain antibody, antibody fragment, chimeric antibody or humanized antibody.

27. The method of claim 25, wherein the antibody is monoclonal antibody 1C9 as produced by hybridoma 1C9 which is deposited with the American Type Culture Collection with Accession Number PTA-8759.

28. The method of claim 25, wherein the influenza A virus to protect the subject from is an H5 subtype of avian influenza virus.

29. The method of claim 28, wherein the avian influenza virus is an H5N1 subtype.

* * * * *